United States Patent
Rao et al.

(10) Patent No.: US 8,758,387 B2
(45) Date of Patent: Jun. 24, 2014

(54) BIOFEEDBACK TRAINING OF ANAL AND RECTAL MUSCLES

(75) Inventors: Satish Sanku Chander Rao, Augusta, GA (US); Muralidhar Nukala Sunil Kumar, Hyderabad (IN)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 13/547,324

(22) Filed: Jul. 12, 2012

(65) Prior Publication Data

US 2013/0018308 A1   Jan. 17, 2013

Related U.S. Application Data

(60) Provisional application No. 61/508,130, filed on Jul. 15, 2011.

(51) Int. Cl.
  *A61M 29/00* (2006.01)
(52) U.S. Cl.
  USPC ........................................ 606/197
(58) Field of Classification Search
  USPC ............. 604/99.04, 101.01, 101.05; 607/197; 606/197
  See application file for complete search history.

(56) References Cited

U.S. PATENT DOCUMENTS

| | | | |
|---|---|---|---|
| 4,019,515 A * | 4/1977 | Kornblum et al. ....... | 604/101.05 |
| 4,932,956 A * | 6/1990 | Reddy et al. ................. | 606/192 |
| 5,452,719 A | 9/1995 | Eisman et al. | |
| 5,483,832 A | 1/1996 | Pauser et al. | |
| 5,674,238 A | 10/1997 | Sample et al. | |
| 5,782,745 A | 7/1998 | Benderev | |
| 5,924,984 A | 7/1999 | Rao | |
| 6,217,529 B1 | 4/2001 | Wax et al. | |
| 6,595,971 B1 * | 7/2003 | von Dyck et al. ............ | 604/334 |
| 6,773,452 B2 * | 8/2004 | Shaker ......................... | 600/587 |
| 7,079,882 B1 | 7/2006 | Schmidt | |
| 7,479,120 B2 | 1/2009 | Gregersen | |
| 7,955,241 B2 | 6/2011 | Hoffman et al. | |
| 8,075,540 B2 | 12/2011 | von Dyck et al. | |
| 8,147,429 B2 | 4/2012 | Mittal et al. | |
| 8,398,669 B2 * | 3/2013 | Kim ............................. | 606/197 |
| 2004/0122341 A1 | 6/2004 | Walsh et al. | |

(Continued)

OTHER PUBLICATIONS

Anorectal Biofeedback Monitors and Probe Specifications, http://www.biosearch.com/anorectal_monitors_spec.html Printed on Oct. 10, 2012.

(Continued)

*Primary Examiner* — Aarti B Berdichevsky
(74) *Attorney, Agent, or Firm* — Bell & Manning, LLC

(57) ABSTRACT

A probe including a housing, a rectal muscle air bag, a rectal tube, an anal muscle air bag, and an anal tube is provided. The rectal muscle air bag mounts to the housing a first distance from a non-insertion end. A rectal tube is connected to the rectal muscle air bag at a first end and to a first pressure sensor at a second end. The anal muscle air bag is mounted to the housing a second distance from the non-insertion end. The anal tube is connected to the anal muscle air bag at a first end and to a second pressure sensor at a second end. The first distance is selected to position the rectal muscle air bag adjacent a rectal muscle, and the second distance is selected to position the anal muscle air bag adjacent an anal muscle when the housing is inserted in the rectum.

41 Claims, 12 Drawing Sheets

(56) References Cited

U.S. PATENT DOCUMENTS

| | | |
|---|---|---|
| 2005/0027313 A1* | 2/2005 | Shaker .......................... 606/197 |
| 2007/0213661 A1 | 9/2007 | Gobel |
| 2008/0300619 A1* | 12/2008 | Isham .......................... 606/197 |
| 2012/0130281 A1* | 5/2012 | Ahn .............................. 600/587 |
| 2012/0215135 A1 | 8/2012 | Galliano et al. |
| 2012/0296272 A1* | 11/2012 | Bidault et al. ........... 604/101.05 |

OTHER PUBLICATIONS

What is Biofeedback Training?, http://www.biosearch.com/biofeedback_training.html, Printed on Oct. 10, 2012.

* cited by examiner

Enter New Patient Information

| Field | Ref |
|---|---|
| Patient Number | 502 |
| Date | 12/29/2004 |
| Social Security No | 504 |
| Patient Name | 506 |
| Address | 508 |
| Area Code | 510 |
| Phone Number | 512 |
| Fax Number | 514 |
| Rectum Max. | 516 |
| Rectum Min. | 518 |
| Anus Max. | 520 |
| Anus Min. | 522 |
| Constipation | 524 |
| Incontinence | 526 |
| Analysis >> | 530/532 |

Fig. 5

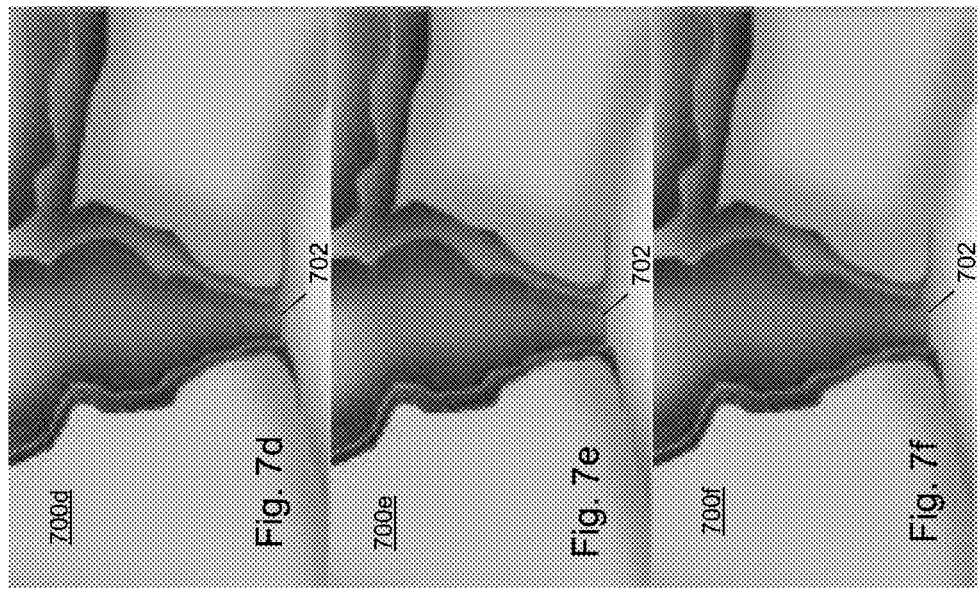
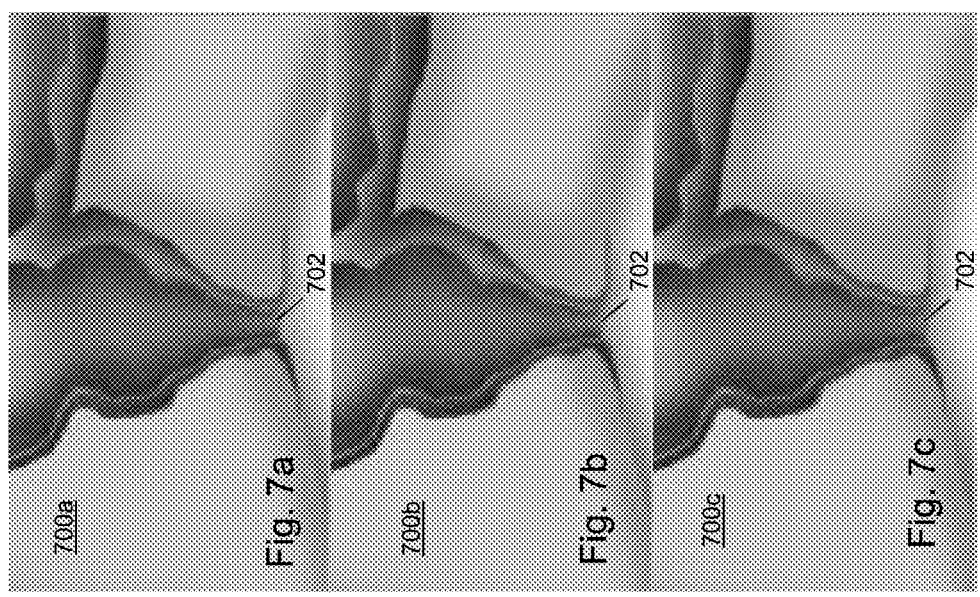

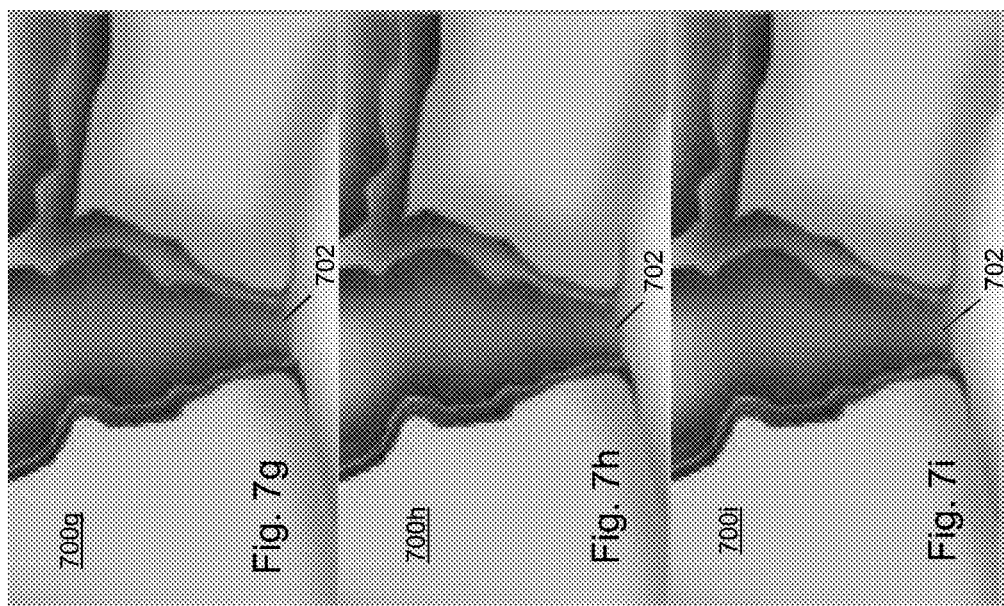

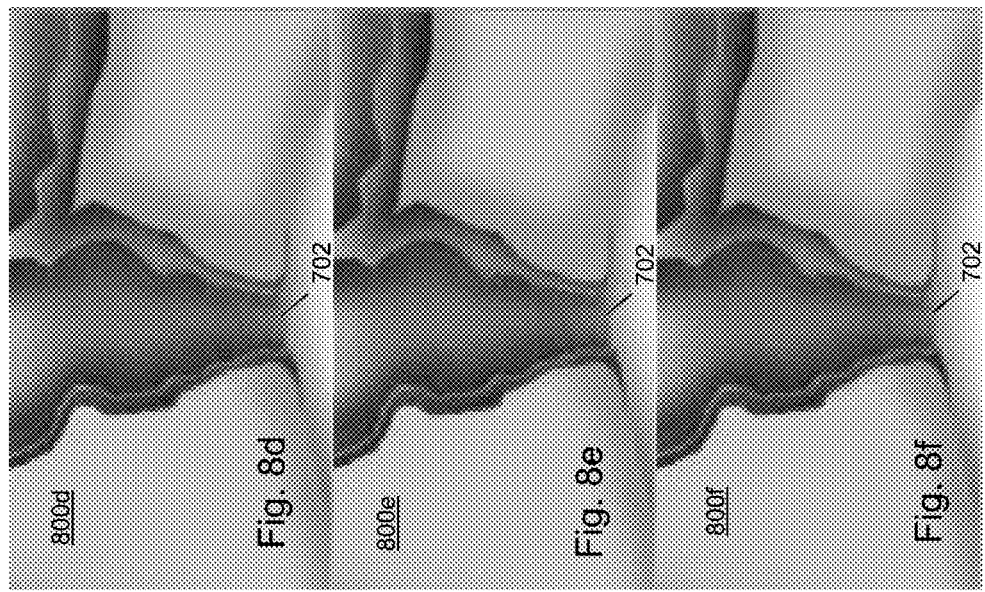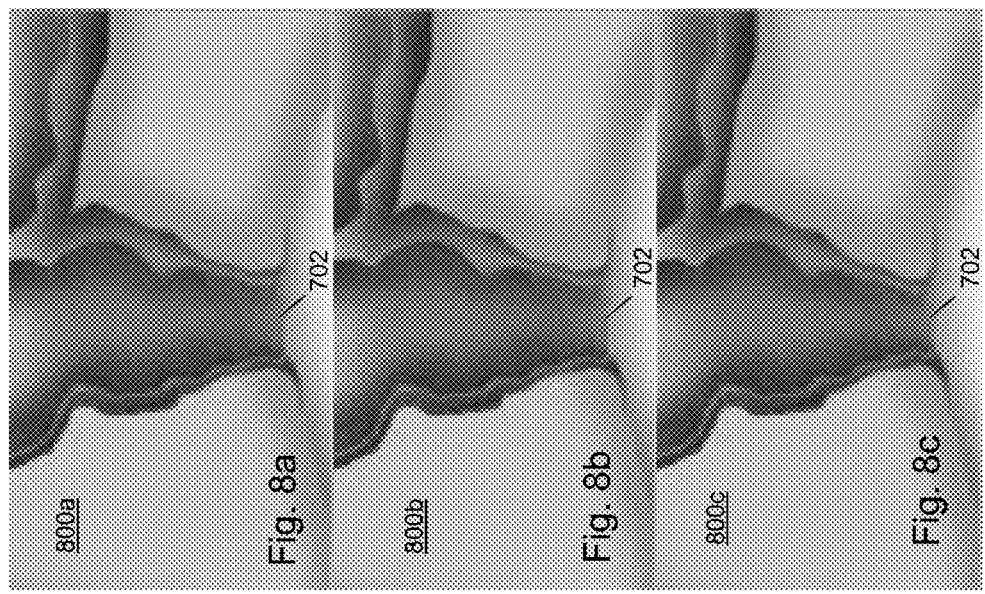

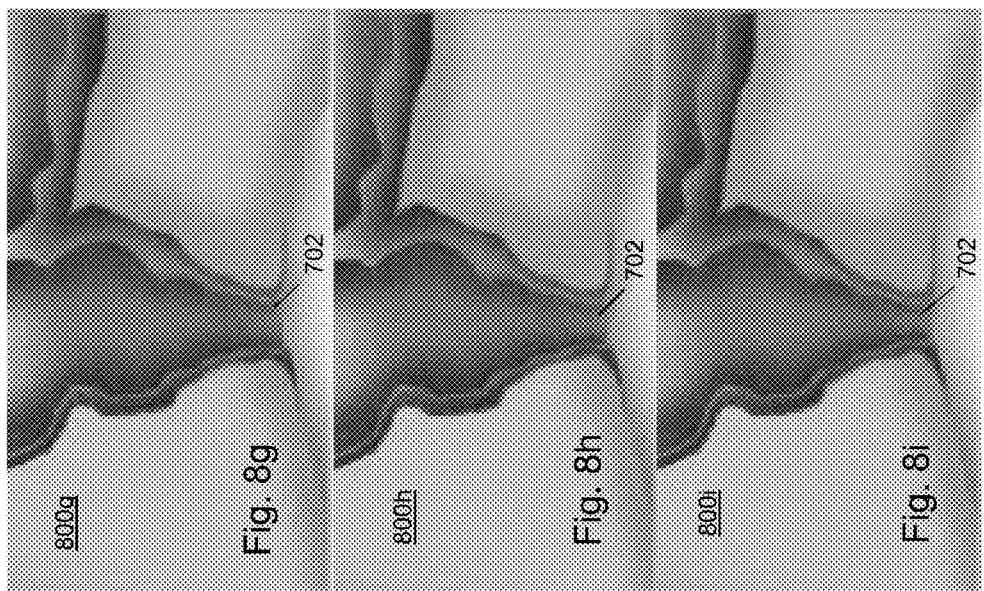

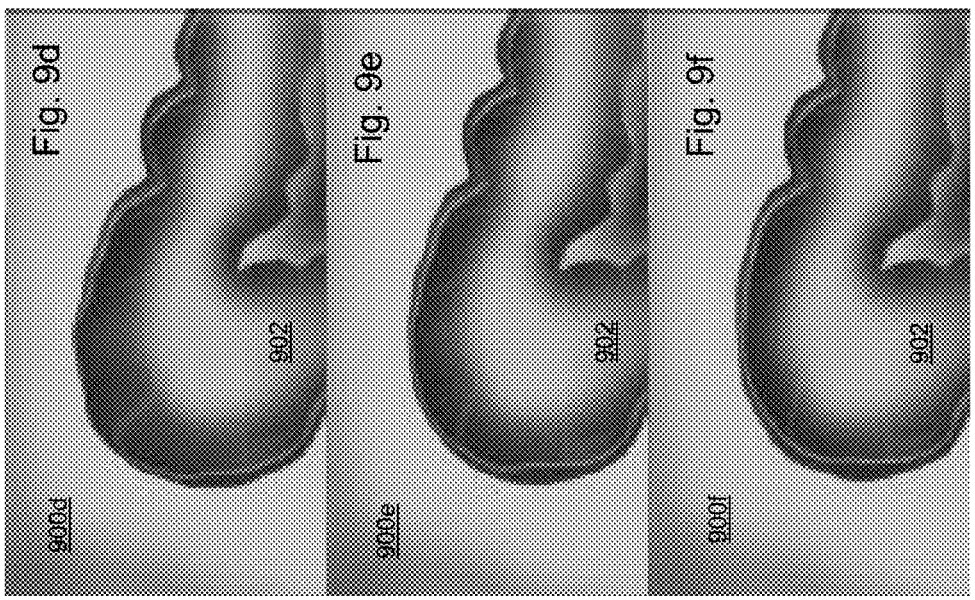
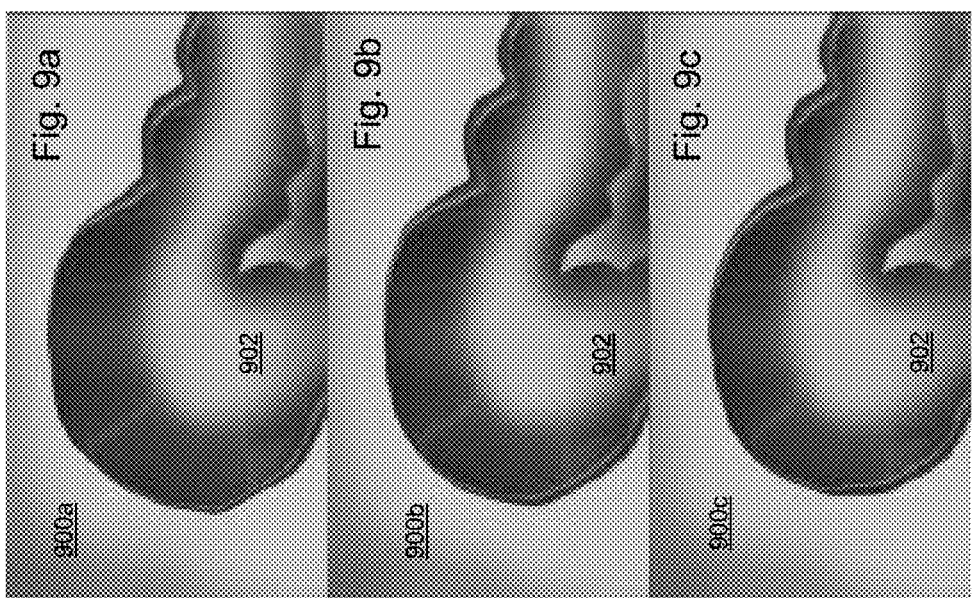

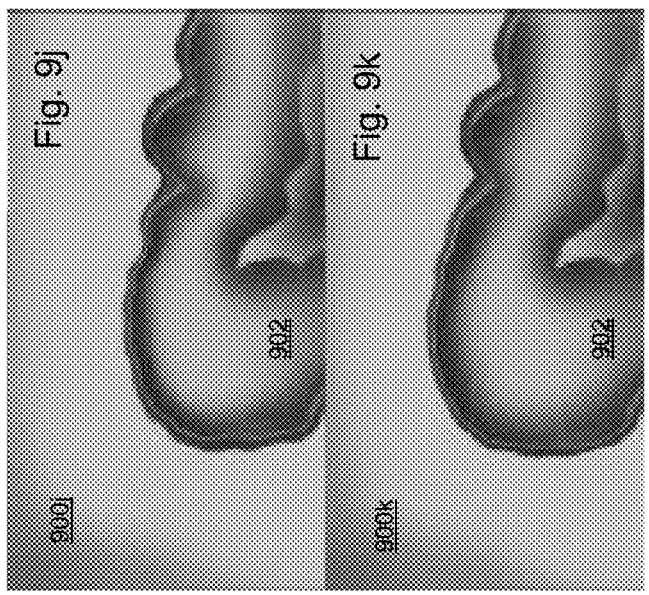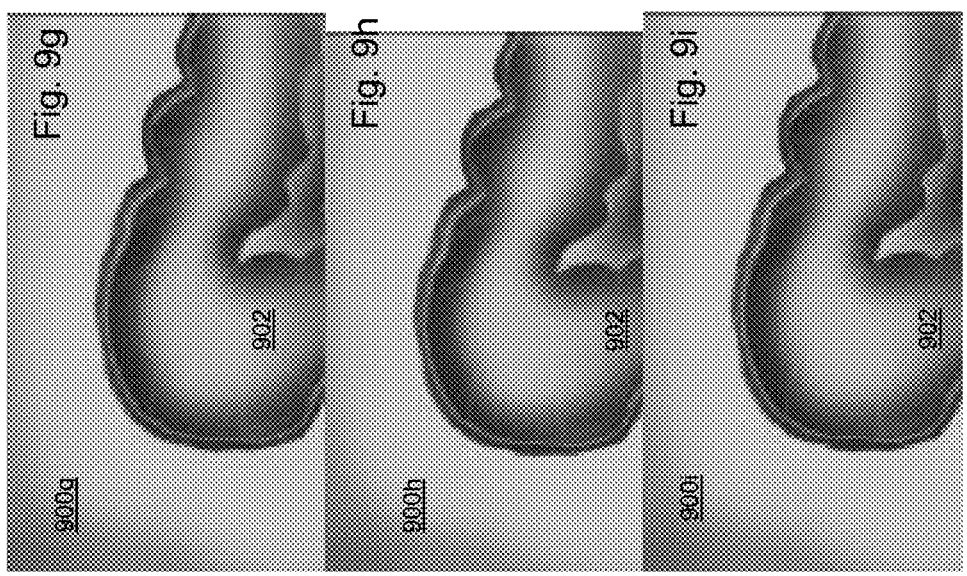

BIOFEEDBACK TRAINING OF ANAL AND RECTAL MUSCLES

CROSS-REFERENCE TO RELATED APPLICATIONS

The present application claims priority to U.S. Provisional Patent Application No. 61/508,130 that was filed Jul. 15, 2011, the entire contents of which are hereby incorporated by reference.

REFERENCE TO GOVERNMENT RIGHTS

This invention was made with government support under Grant No. R01 DK057100 awarded by the NIH. The Government has certain rights in the invention.

BACKGROUND

Constipation and leakage of stool (fecal incontinence) are common bowel problems. Sometimes they are caused by malfunction of anal and rectal muscles or weakness of these muscles. Biofeedback therapy is an instrument-guided treatment program designed to improve the coordination and strength of these muscles. Incontinence training is a method of improving bowel function in patients with stool leakage. The greater the muscle contraction, the greater the activation of displayed lights on the instrument when the instrument is switched into the incontinence training mode. Similarly, for patients with constipation, the greater the muscle relaxation, the greater the activation of displayed lights on the instrument when the instrument is switched into the constipation mode.

SUMMARY

In an example embodiment, a probe is provided. The probe includes a housing, a rectal muscle air bag, a rectal tube, an anal muscle air bag, and an anal tube. The housing is configured for insertion into a rectum and has an insertion end and a non-insertion end. The rectal muscle air bag is mounted to the housing a first distance from the non-insertion end. The first distance is selected to position the rectal muscle air bag adjacent a rectal muscle when the housing is inserted in the rectum. The rectal tube is connected to the rectal muscle air bag at a first end of the rectal tube to provide a first vent for the rectal muscle air bag. The rectal tube is further configured for connection to a first pressure sensor at a second end of the rectal tube. The anal muscle air bag is mounted to the housing a second distance from the non-insertion end. The second distance is selected to position the anal muscle air bag adjacent an anal muscle when the housing is inserted in the rectum. The anal tube is connected to the anal muscle air bag at a first end of the anal tube to provide a first vent for the anal muscle air bag. The anal tube is further configured for connection to a second pressure sensor at a second end of the anal tube.

In another example embodiment, a system is provided. The system includes a housing, a first pressure sensor, a second pressure sensor, a probe, and a processor. The first pressure sensor is mounted to the housing and is configured to measure a rectal muscle pressure. The second pressure sensor is mounted to the housing and is configured to measure an anal muscle pressure. The probe includes a probe housing, a rectal muscle air bag, a rectal tube, an anal muscle air bag, and an anal tube. The probe housing is configured for insertion into a rectum and includes an insertion end and a non-insertion end. The rectal muscle air bag is mounted to the probe housing a first distance from the non-insertion end, wherein the first distance is selected to position the rectal muscle air bag adjacent a rectal muscle when the probe housing is inserted in the rectum. The rectal tube is connected to the rectal muscle air bag at a first end of the rectal tube and to the first pressure sensor at a second end of the rectal tube. The anal muscle air bag is mounted to the probe housing a second distance from the non-insertion end, wherein the second distance is selected to position the anal muscle air bag adjacent an anal muscle when the probe housing is inserted in the rectum. The anal tube is connected to the anal muscle air bag at a first end of the anal tube and to the second pressure sensor at a second end of the anal tube. The processor is mounted to the housing and is configured to control presentation of the measured rectal muscle pressure and the measured anal muscle pressure.

In still another example embodiment, a system is provided. The system includes, but is not limited to, a first housing, a first pressure sensor, a second pressure sensor, a probe, a first processor, a first communication interface, a second processor, a second communication interface, and a computer-readable medium operably coupled to the second processor. The first pressure sensor is mounted to the first housing and is configured to measure a rectal muscle pressure. The second pressure sensor is mounted to the first housing and is configured to measure an anal muscle pressure. The probe includes a probe housing, a rectal muscle air bag, a rectal tube, an anal muscle air bag, and an anal tube. The probe housing is configured for insertion into a rectum and includes an insertion end and a non-insertion end. The rectal muscle air bag is mounted to the probe housing a first distance from the non-insertion end, wherein the first distance is selected to position the rectal muscle air bag adjacent a rectal muscle when the probe housing is inserted in the rectum. The rectal tube is connected to the rectal muscle air bag at a first end of the rectal tube and to the first pressure sensor at a second end of the rectal tube. The anal muscle air bag is mounted to the probe housing a second distance from the non-insertion end, wherein the second distance is selected to position the anal muscle air bag adjacent an anal muscle when the probe housing is inserted in the rectum. The anal tube is connected to the anal muscle air bag at a first end of the anal tube and to the second pressure sensor at a second end of the anal tube. The first processor is mounted to the first housing and is configured to control presentation of the measured rectal muscle pressure and the measured anal muscle pressure. The first communication interface is operably coupled to the first processor and is configured to send the measured rectal muscle pressure and the measured anal muscle pressure to a second communication interface. The second processor is mounted to a second housing. The second communication interface is operably coupled to the second processor and is configured to receive the measured rectal muscle pressure and the measured anal muscle pressure from the first communication interface. The computer-readable medium has computer-readable instructions stored thereon that, when executed by the second processor, cause the system to control presentation of a graphical representation of the received rectal muscle pressure and the received anal muscle pressure in a display.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 5 is a first user interface window presented under control of a biofeedback performance application of the interfaced computing device of FIG. 3 in accordance with an illustrative embodiment.

FIGS. 7a-7i depict an anus muscle movement for a constipation mode presented under control of the biofeedback performance application of the interfaced computing device of FIG. 3 in accordance with an illustrative embodiment.

FIGS. 8a-8i depict an anus muscle movement for an incontinence mode presented under control of the biofeedback performance application of the interfaced computing device of FIG. 3 in accordance with an illustrative embodiment.

FIGS. 9a-9k depict a rectal muscle movement presented under control of the biofeedback performance application of the interfaced computing device of FIG. 3 in accordance with an illustrative embodiment.

DETAILED DESCRIPTION

Figure 1:
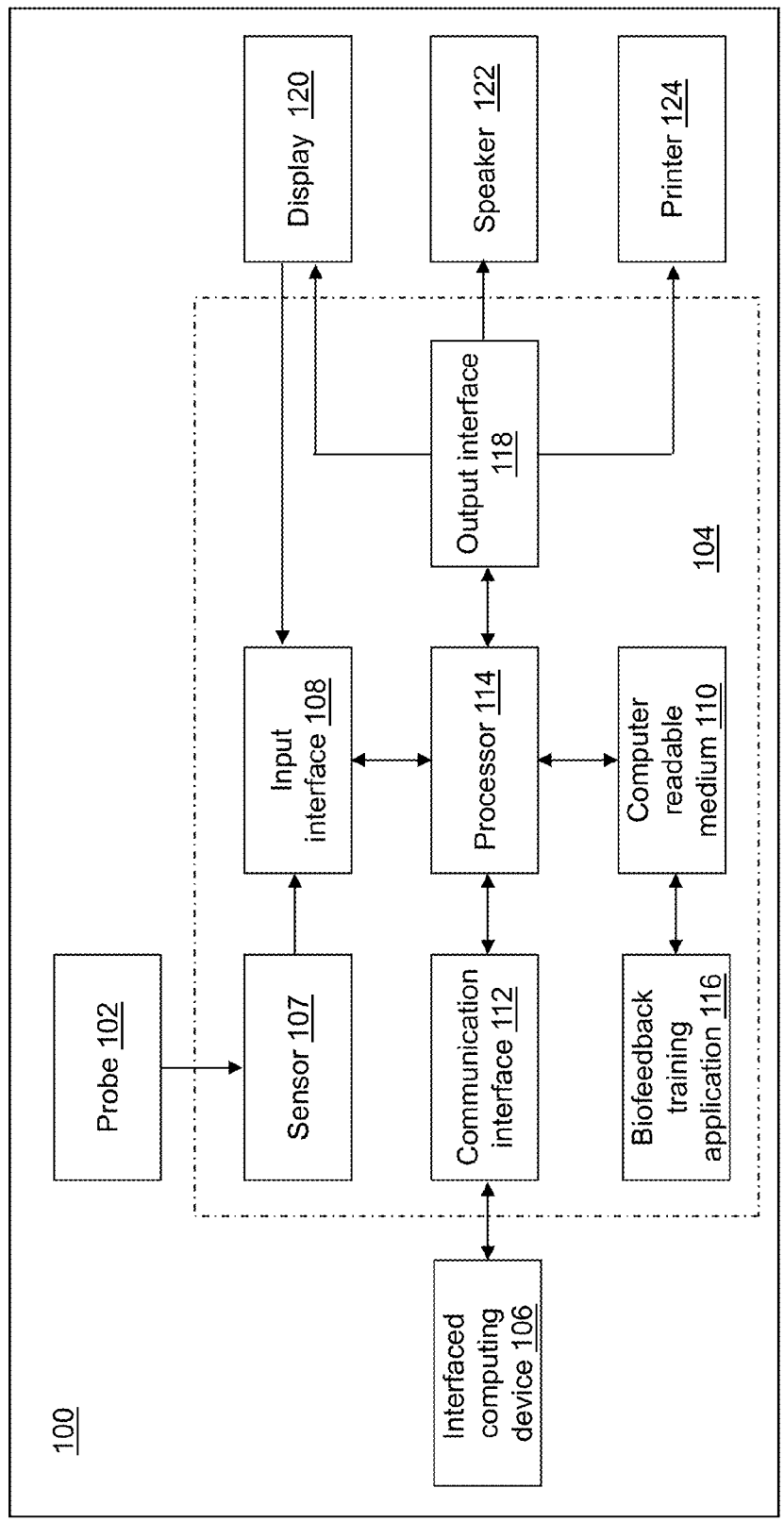
FIG. 1 depicts a block diagram of a biofeedback training system in accordance with an illustrative embodiment.

With reference to FIG. 1, a block diagram of a biofeedback training system 100 is shown in accordance with an illustrative embodiment. In an illustrative embodiment, biofeedback training system 100 may include a probe 102, a monitor 104, an interfaced computing device 106, a display 120, a speaker 122, and a printer 124. The components of biofeedback training system 100 may be positioned in a single location, a single facility, and/or may be remote from one another. Biofeedback training system 100 may be integrated in one or more computing devices. One or more components of biofeedback training system 100 may be integrated into a single computing device. One or more of the components of biofeedback training system 100 may be connected directly, for example, using a cable for transmitting information between systems. One or more of the components of biofeedback training system 100 may be connected using network 108. For example, monitor 104 and interfaced computing device 106 may be connected directly through a wireless or a wired communication interface or may be connected through a network. The network can be any type of wired and/or wireless public or private network including a cellular network, a local area network, a wide area network such as the Internet, etc. The network further may be comprised of sub-networks and consist of any number of devices.

Figure 2:
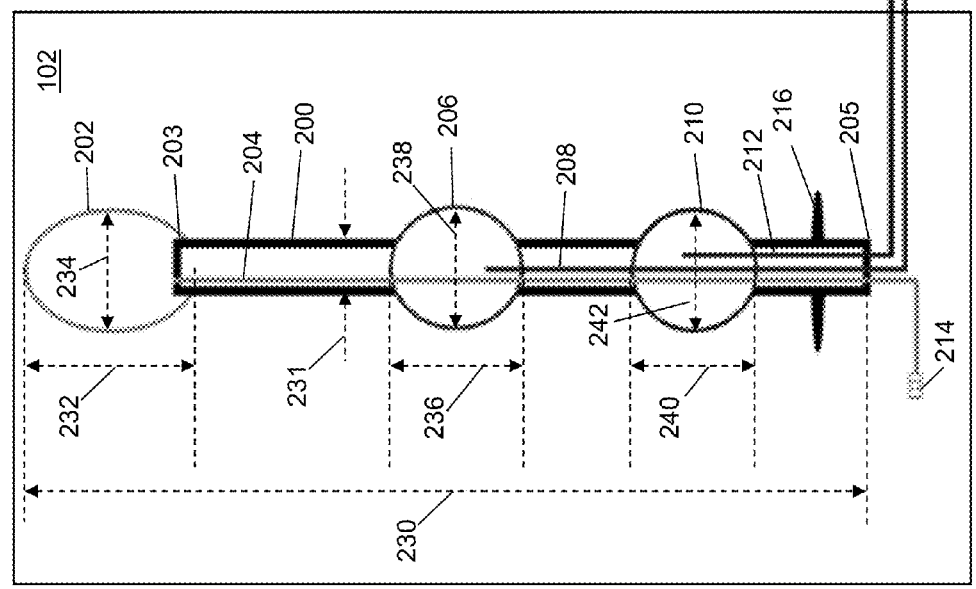
FIG. 2 depicts a schematic diagram of a probe of the biofeedback training system of FIG. 1 in accordance with an illustrative embodiment.
Figure 2:
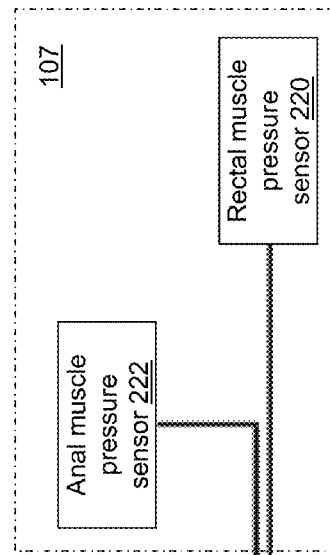

With reference to FIG. 2, probe 102 may include a housing 200, a stool stimulation air bag 202, a rectal muscle air bag 206, and an anal muscle air bag 210. Housing 200 may be sized and shaped for comfortable insertion into a rectum of a patient. Housing 200 may be generally cylindrical in shape and include an insertion end 203 of probe 102 and a non-insertion end 205 of probe 102, which is opposite the insertion end 203. A stop edge 216 extending from housing 200 near non-insertion end 205 is sized to prevent further insertion of probe 102 into the rectum of the patient. Housing 200 may be formed of a variety of materials. For example, housing 200 may be formed of rubber silicone.

In the illustrative embodiment of FIG. 2, housing 200 has a housing length 230 of approximately 145 millimeters (mm) and a housing diameter 231 of approximately 10.5 mm; stool stimulation air bag 202 has a stool stimulation air bag length 232 of approximately 25 mm and a stool stimulation air bag diameter 234 of approximately 15.7 mm; rectal muscle air bag 206 has a rectal muscle air bag length 236 of approximately 15 mm and a rectal muscle air bag diameter 238 of approximately 15.3 mm; and anal muscle air bag 210 has an anal muscle air bag length 240 of approximately 15 mm and an anal muscle air bag diameter 242 of approximately 15.3 mm.

Stool stimulation air bag 202 is mounted to insertion end 203 of probe 102. A conduit 204 connects stool stimulation air bag 202 with a source of fluid such as air or water used to inflate stool stimulation air bag 202. A connector 214 connects to a first end of conduit 204 and is configured for connection to the fluid source. Connector 214 may include a valve to control the fluid flow into and out of conduit 204. For example, after inflation of stool stimulation air bag 202, connector 214 may allow the deflation of stool stimulation air bag 202 through the exertion of pressure on stool stimulation air bag 202. Inflation of stool stimulation air bag 202 may simulate the sensation of fecal mass in a rectum of the patient.

Rectal muscle air bag 206 is mounted to housing 200 at a first distance from stop edge 216. The first distance is selected so that rectal muscle air bag 206 is positioned adjacent the rectal muscle of the patient when probe 102 is inserted into the rectum. A pressure fluctuation generated by a contraction of the rectal muscle of the patient causes a deflation of rectal muscle air bag 206. A rectal tube 208 connects rectal muscle air bag 206 to a rectal muscle pressure sensor 220 and provides a transmission path for fluid flow between rectal muscle air bag 206 and rectal muscle pressure sensor 220. Thus, rectal tube 208 acts as a vent for rectal muscle air bag 206. Rectal muscle pressure sensor 220 may include a piezoelectric device configured to measure the pressure exerted on rectal muscle air bag 206 by measuring the dynamic pressure within rectal tube 208.

Anal muscle air bag 210 is mounted to housing 200 at a second distance from stop edge 216. The second distance is selected so that anal muscle air bag 210 is positioned adjacent the anal muscle of the patient when probe 102 is inserted into the rectum. A pressure fluctuation generated by a contraction of the anal muscle of the patient causes a deflation of anal muscle air bag 210. An anal tube 212 connects anal muscle air bag 210 to an anal muscle pressure sensor 222 and provides a transmission path for fluid flow between anal muscle air bag 210 and anal muscle pressure sensor 222. Thus, anal tube 212 acts as a vent for anal muscle air bag 210. Anal muscle pressure sensor 222 may include a piezoelectric device configured to measure the pressure exerted on anal muscle air bag 210 by measuring the dynamic pressure within anal tube 212.

With continuing reference to FIG. 1, monitor 104 may include a sensor 107, an input interface 108, a computer-readable medium 110, a communication interface 112, a processor 114, a biofeedback training application 116, and an output interface 118. Different and additional components may be incorporated into monitor 104. For example, monitor 104 may include a battery. Sensor 107 may include rectal muscle pressure sensor 220 and/or anal muscle pressure sensor 222. Sensor 107 detects a dynamic pressure within rectal tube 208 and/or anal tube 212. The detected dynamic pressure may be amplified, sampled, and converted from an analog value to a digital value using an analog-to-digital converter. The digital value of the detected dynamic pressure may be input to processor 114 through input interface 108 and/or stored in computer-readable medium 110 through input interface 108, for example, using a wire or other electronic transmission means.

Input interface 108 also may provide an interface for receiving information from a user for entry into monitor 104 as known to those skilled in the art. The user of monitor 104 and/or interfaced computing device 106 may be the patient and/or a clinician. As used herein, the term "clinician" refers to any employee or agent of any type of medical facility including but not limited to doctors, nurses, therapists, etc. Input interface 108 may use various input technologies including, but not limited to, a keyboard, a pen and touch screen, a mouse, a track ball, a touch screen, a keypad, one or more buttons, etc. to allow the user to enter information into monitor 104 or to make selections presented in a user interface displayed on display 120. The same interface may support both input interface 108 and output interface 118. For example, a touch screen both allows user input and presents output to the user. Monitor 104 may have one or more input interfaces that use the same or a different input interface technology.

For example, monitor 104 may include a sensitivity adjustment control to allow the user to adjust the sensitivity of sensor 107. Monitor 104 may include separate adjustment controls for rectal muscle pressure sensor 220 and anal muscle pressure sensor 222. For example, monitor 104 may provide three sensitivity levels that are selectable by the user. In an illustrative embodiment, in an initial stage, a high sensitivity level may be selected. After the display is presented at the high sensitivity level, a medium sensitivity level may be selected. After the display is presented at the medium sensitivity level, a low sensitivity level may be selected.

Computer-readable medium 110 is an electronic holding place or storage for information so that the information can be accessed by processor 114 as known to those skilled in the art. Computer-readable medium 110 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., CD, DVD, . . . ), smart cards, flash memory devices, etc. Monitor 104 may have one or more computer-readable media that use the same or a different memory media technology. Monitor 104 also may have one or more drives that support the loading of a memory media such as a CD or DVD.

Communication interface 112 provides an interface for receiving and transmitting data between devices using various protocols, transmission technologies, and media as known to those skilled in the art. Communication interface 112 may support communication using various transmission media that may be wired or wireless. Monitor 104 may have one or more communication interfaces that use the same or a different communication interface technology. Data and messages may be transferred between interfaced computing device 106 and/or a monitor 104 using communication interface 112.

Processor 114 executes instructions as known to those skilled in the art. The instructions may be carried out by a special purpose computer, logic circuits, or hardware circuits. Thus, processor 114 may be implemented in hardware, firmware, or any combination of these methods and/or in combination with software. The term "execution" is the process of running an application or the carrying out of the operation called for by an instruction. The instructions may be written using one or more programming language, scripting language, assembly language, etc. Processor 114 executes an instruction, meaning that it performs/controls the operations called for by that instruction. Processor 114 operably couples with output interface 118, with input interface 108, with computer-readable medium 110, and with communication interface 112 to receive, to send, and to process information. Processor 114 may retrieve a set of instructions from a permanent memory device and copy the instructions in an executable form to a temporary memory device that is generally some form of RAM. Monitor 104 may include a plurality of processors that use the same or a different processing technology.

Biofeedback training application 116 performs operations associated with biofeedback therapy to improve the coordination and strength of the anal and rectal muscles. Some or all of the operations described herein may be embodied in biofeedback training application 116. The operations may be implemented using hardware, firmware, software, or any combination of these methods. With reference to the example embodiment of FIG. 1, biofeedback training application 116 is implemented in software (comprised of computer-readable and/or computer-executable instructions) stored in computer-readable medium 110 and accessible by processor 114 for execution of the instructions that embody the operations of biofeedback training application 116. Biofeedback training application 116 may be written using one or more programming languages, assembly languages, scripting languages, etc.

Output interface 118 provides an interface for outputting information for review by the user of monitor 104. For example, output interface 118 may include an interface to display 120, speaker 122, printer 124, etc. Display 120 may be a thin film transistor display, a light emitting diode display, a liquid crystal display, or any of a variety of different displays known to those skilled in the art. Speaker 122 may be any of a variety of speakers as known to those skilled in the art. Printer 124 may be any of a variety of printers as known to those skilled in the art. Monitor 104 may have one or more output interfaces that use the same or a different interface technology. Display 120, speaker 122, and/or printer 124 further may be accessible to monitor 104 through communication interface 112. Display 120, speaker 122, and/or printer 124 further may be integrated with monitor 104.

Figure 3:
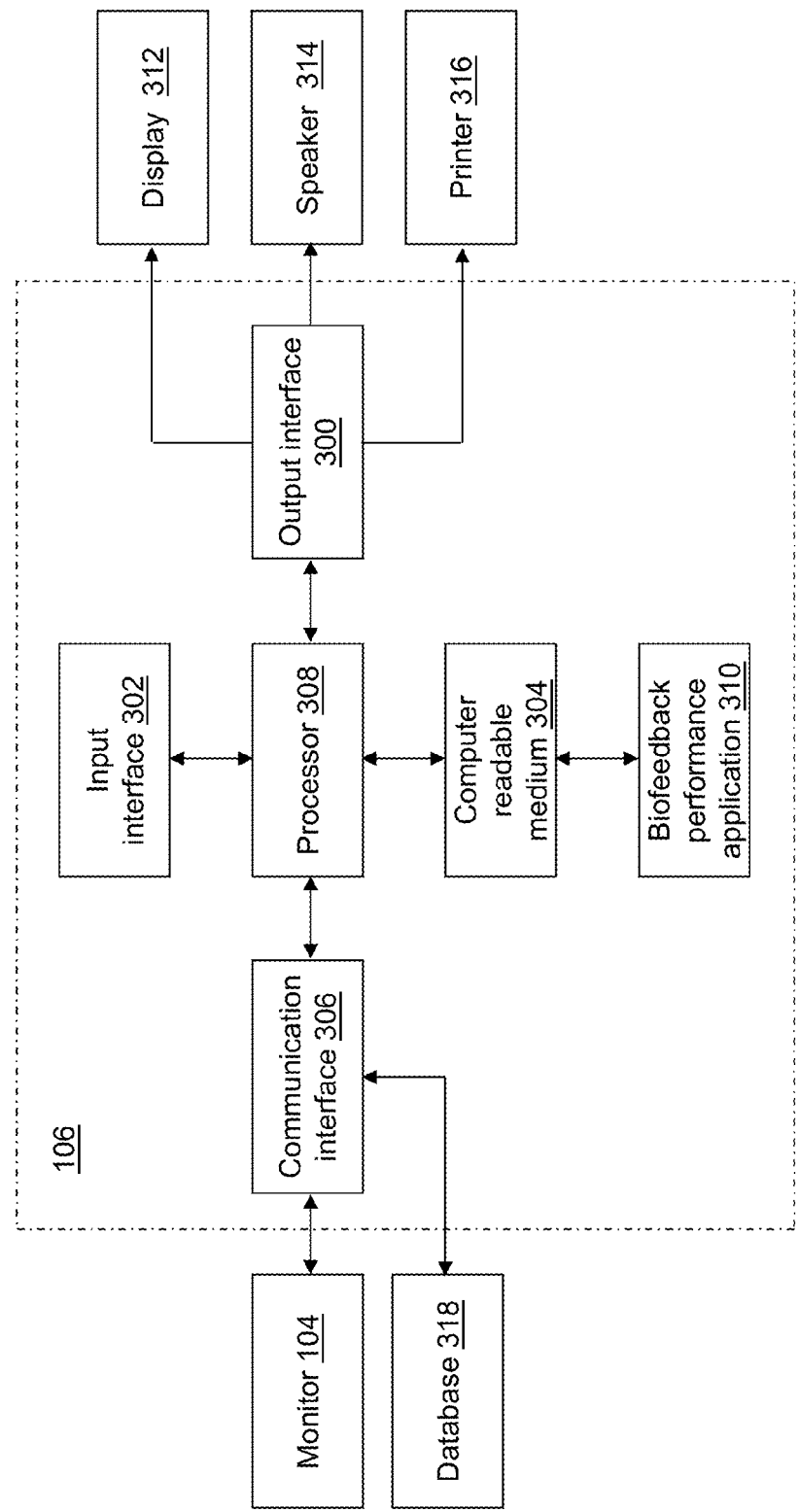
FIG. 3 depicts a block diagram of an interfaced computing device of the biofeedback training system of FIG. 1 in accordance with an illustrative embodiment.

With reference to FIG. 3, interfaced computing device 106 may include a second output interface 300, a second input interface 302, a second computer-readable medium 304, a second communication interface 306, a second processor 308, and a biofeedback performance application 310. Different and additional components may be incorporated into interfaced computing device 106.

Interfaced computing device 106 may include one or more computing devices. The one or more computing devices may send and receive signals from one or more monitors through the network or a direct wired or wireless communication interface. Interfaced computing device 106 can include any number and type of computing devices. The one or more computing devices may include computers of any form factor such as a personal digital assistant, a desktop, a laptop, an integrated messaging device, a cellular telephone, a smart phone, a pager, etc. Interfaced computing device 106 may receive information generated by biofeedback training application 116 for storage in a database 318. Interfaced computing device 106 may communicate with other computing devices.

Database 318 is a data repository for biofeedback training system 100. Database 318 may include a plurality of databases that may be organized into multiple database tiers to improve data management and access. Database 318 may utilize various database technologies and a variety of different formats as known to those skilled in the art including a file system, a relational database, a system of tables, a structured query language database, etc. Database 318 may be implemented as a single database or as multiple databases stored in different storage locations distributed over the Internet or other heterogeneous storage infrastructures.

Second output interface 300 provides the same or similar functionality as that described with reference to output interface 118 of monitor 104. Second input interface 302 provides the same or similar functionality as that described with reference to input interface 108 of monitor 104. Second computer-readable medium 304 provides the same or similar functionality as that described with reference to computer-readable medium 110 of monitor 104. Second communication interface 306 provides the same or similar functionality as that described with reference to communication interface 112 of monitor 104. Second processor 308 provides the same or similar functionality as that described with reference to processor 114 of monitor 104. Second display 312 provides the same or similar functionality as that described with reference to display 120. Second speaker 314 provides the same or similar functionality as that described with reference to speaker 122. Second printer 316 provides the same or similar functionality as that described with reference to printer 124.

Biofeedback training application 116 receives the value of the dynamic pressure detected by rectal muscle pressure sensor 220 and anal muscle pressure sensor 222 and converts the received value to a presentation value. Biofeedback training application 116 may receive dynamic pressure values from rectal muscle pressure sensor 220 and anal muscle pressure sensor 222 essentially simultaneously (within a few milliseconds). The dynamic pressure may be presented using display 120, speaker 122, printer 124, second display 312, second speaker 314, and/or second printer 316. A variety of methods may be used to present the dynamic pressure information to the user. For example, a bar graph of one or more colors may be used to indicate the muscle performance. Biofeedback training application 116 may send the dynamic pressure information with information identifying the patient and/or the user (if different), the time, and date to interfaced computing device 106.

Biofeedback training application 116 may support one or more operational modes that are user selectable, for example, using an operational mode control included on monitor 104. In an illustrative embodiment, a first mode may be a constipation mode, and a second mode may be an incontinence mode. A default mode may be the constipation mode. In the constipation mode, probe 102 is inserted into the patient and monitor 104 is switched on. At power on, rectal muscle pressure sensor 220 and anal muscle pressure sensor 222 may be automatically calibrated while all of the displays remain off. Display 120 presents the dynamic pressure information when the patient starts releasing the pressure on rectal muscle air bag 206 and anal muscle air bag 210. Display 120 provides a clear picture of the movement of the rectum and the anus muscles to the patient during the bio-feedback training.

In the incontinence mode, an indicator light on monitor 104 may indicate that the mode has been selected. At power on, rectal muscle pressure sensor 220 and anal muscle pressure sensor 222 may be automatically calibrated without inserting probe 102 into the patient. After inserting probe 102, display 120 presents the dynamic pressure information when the patient starts squeezing probe 120 by contracting the anus muscles during the bio-feedback training. Any undesirable contraction of the rectal muscles is also displayed, and if present, the visual feedback is used to correct this disfunction.

Figure 4:
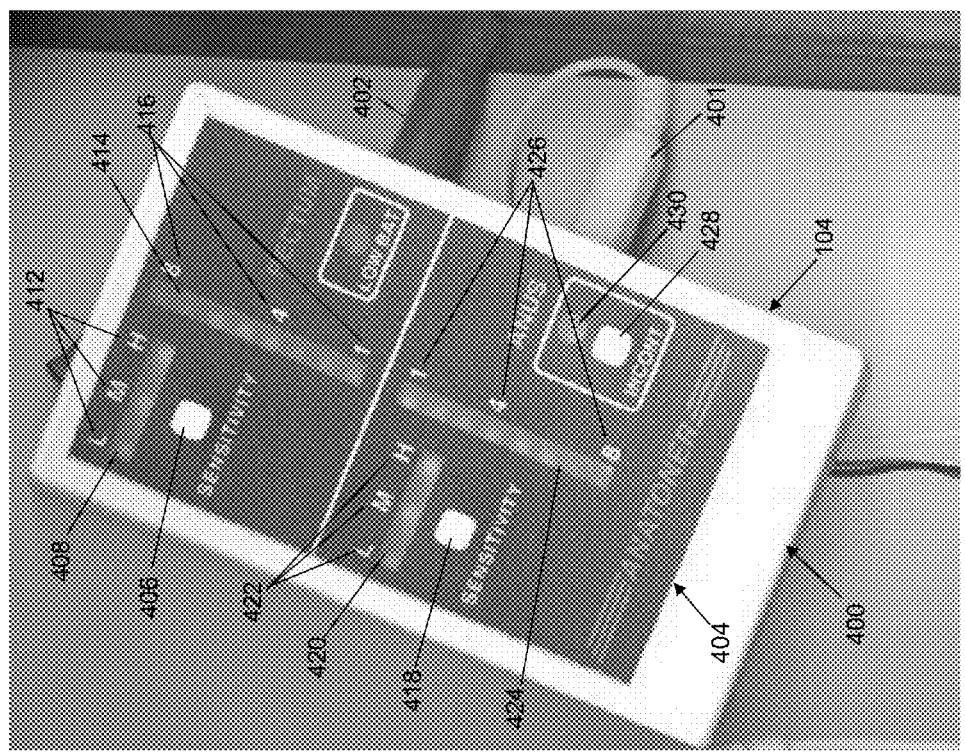
FIG. 4 is a photograph of a probe and monitor of the biofeedback training system of FIG. 1 in accordance with an illustrative embodiment.

With reference to FIG. 4, probe 102 is shown connected to monitor 104 in accordance with an illustrative embodiment. In the illustrative embodiment of FIG. 4, monitor 104 includes a housing 400 through which monitor 104 is connected to probe 102. Housing 400 includes a first input interface (not shown) for an anus connector 401 and a second input interface (not shown) for a rectum connector 402. Anus connector 401 connects anal muscle air bag 210 of probe 102 to anal muscle pressure sensor 222 mounted within housing 400 of monitor 104. Rectum connector 402 connects rectal muscle air bag 206 of probe 102 to rectal muscle pressure sensor 220 mounted within housing 400 of monitor 104.

Monitor 104 further includes an input/output (I/O) interface 404. In the illustrative embodiment of FIG. 4, I/O interface 404 includes a rectal sensitivity selector button 406, a rectal sensitivity indicator 408, rectal sensitivity level indicators 412, a rectal muscle output indicator 414, rectal output level indicators 416, an anal sensitivity selector button 418, an anal sensitivity indicator 420, anal sensitivity level indicators 422, an anal muscle output indicator 424, anal output level indicators 426, an anal mode selector button 428, and an anal mode indicator 430. Different and additional or fewer buttons, indicators, selectors, etc. may be incorporated into I/O interface 404. Additionally, the arrangement of the buttons, indicators, selectors, etc. may be other than that shown in the illustrative embodiment.

Rectal sensitivity selector button 406 is a sensitivity adjustment control that allows the user to adjust the sensitivity of rectal muscle pressure sensor 220. For example, in the illustrative embodiment, I/O interface 404 allows the user to select from three sensitivity levels: low, medium, and high. As a result, rectal sensitivity indicator 408 may include three light emitting diodes (LEDs) and three rectal sensitivity level indicators 412, "L", "M", and "H". The LED associated with the selected sensitivity level is switched on to indicate the selection of that sensitivity level. Rectal muscle output indicator 414 provides an indication of the rectal muscle response as measured by rectal muscle pressure sensor 220 based on a pressure exerted on rectal muscle air bag 206 by the user after insertion of probe 102 and turning on of monitor 104. Rectal muscle output indicator 414 may include a plurality of LEDs of various colors to indicate the rectal muscle response based on the sensitivity level entered by the patient and/or by the clinician using I/O interface 404. Rectal output level indicators 416 may include a plurality of numerical values associated with the corresponding LED.

In an illustrative embodiment, biofeedback training application 116 calculates the rectal muscle response based on a sensitivity level entered by the user using I/O interface 404. For example, the response may be calculated as $R_r = (ADC_r - A_{0r})/2S_r$, where $R_r$ is the rectal muscle response value used to determine the number of LEDs switched on in rectal muscle output indicator 414, $ADC_r$ is the digital value of the rectal muscle response as measured by rectal muscle pressure sensor 220, $A_{0r}$ is an auto zero value for rectal muscle pressure sensor 220, and $S_r$ is a numerical value associated with the sensitivity level selected by the user using rectal sensitivity selector button 406.

Anal sensitivity selector button 418 is a sensitivity adjustment control that allows the user to adjust the sensitivity of anal muscle pressure sensor 222. For example, in the illustrative embodiment, I/O interface 404 allows the user to select from three sensitivity levels: low, medium, and high. As a result, anal sensitivity indicator 420 may include three light emitting diodes (LEDs) and three anal sensitivity level indicators 422, "L", "M", and "H". The LED associated with the selected sensitivity level is switched on to indicate the selection of that sensitivity level. Anal muscle output indicator 424 provides an indication of the anal muscle response as measured by anal muscle pressure sensor 222 based on a pressure exerted on anal muscle air bag 210 by the user after insertion of probe 102 and turning on of monitor 104. Anal muscle output indicator 424 may include a plurality of LEDs of various colors to indicate the anal muscle response based on the sensitivity level entered by the user and/or by the clinician using I/O interface 404. Anal output level indicators 426 may include a plurality of numerical values associated with the corresponding LED. Anal mode selector button 428 allows the user to select between the incontinence and the constipation modes. In an illustrative embodiment, anal mode indicator 430 includes an LED that is switched on when monitor 104 is switched into the incontinence mode by the user.

In an illustrative embodiment, biofeedback training application 116 calculates the anal muscle response based on a first sensitivity level entered by the user using I/O interface 404 and a second sensitivity level entered by the clinician. For example, the response may be calculated as $R_a=(ADC_a-A_{0a})/S_a$ when the mode selected is the incontinence mode, where $R_a$ is the anal muscle response value used to determine the number of LEDs switched on in anal muscle output indicator 424, $ADC_a$ is the digital value of the anal muscle response as measured by anal muscle pressure sensor 222, $A_{0a}$ is an auto zero value for anal muscle pressure sensor 222, and $S_a$ is a numerical value associated with the total sensitivity level selected by the user using anal sensitivity selector button 418 and by the clinician and is the sum of the first sensitivity level and the second sensitivity level. The response may be calculated as $R_a=(A_{0a}-ADC_a)/S_a$ when the mode selected is the constipation mode.

Similar to biofeedback training application 116, biofeedback performance application 310 may perform operations associated with biofeedback therapy to improve the coordination and strength of the anal and rectal muscles. Some or all of the operations described herein may be embodied in biofeedback performance application 310. The operations may be implemented using hardware, firmware, software, or any combination of these methods. With reference to the example embodiment of FIG. 3, biofeedback performance application 310 is implemented in software (comprised of computer-readable and/or computer-executable instructions) stored in computer-readable medium 304 and accessible by processor 308 for execution of the instructions that embody the operations of biofeedback training application 116. Biofeedback performance application 310 may be written using one or more programming languages, assembly languages, scripting languages, etc.

Biofeedback performance application 310 may receive biofeedback information from one or more monitors and store the received information associated with a specific user to evaluate the progress of a plurality of users. Biofeedback performance application 310 further may present information to a clinician summarizing the muscle performance of one or more of the users over time. For example, biofeedback performance application 310 may control the display of the movement of the anal and rectum muscles graphically to improve the patient performance during physiotherapy.

With reference to FIG. 5, a first user interface window 500 is shown in accordance with an illustrative embodiment after the user accesses/executes biofeedback performance application 310 at interfaced computing device 106. For example, first user interface window 500 may be presented on display 312 after the clinician selects an option to enter new patient information from an initial user interface window presented on display 312 under control of biofeedback performance application 310 as understood by a person of skill in the art. First user interface window 500 includes patient information organized to allow access to medical information associated with a patient and may be designed in various manners to provide a rapid and logical access to the patient's information by the clinician.

In the illustrative embodiment, first user interface window 500 includes a patient number field 502, a patient identifier number field 504, a patient name field 506, a patient address field 508, a patient area code field 510, a patient phone number field 512, a patient facsimile number field 514, a patient rectum maximum field 516, a patient rectum minimum field 518, a patient anus maximum field 520, a patient anus minimum field 522, a constipation mode radio button 524, an incontinence mode radio button 526, an update record button 528, an analysis button 530, and a save button 532.

The numeric values entered in patient rectum maximum field 516 and patient rectum minimum field 518 are the maximum and minimum values used for rectum muscle performance analysis and are used to determine a number of rectal cycles completed. For example, the patient rectum muscle performance value starts from the value entered in patient rectum minimum field 518. When the patient rectum muscle performance value reaches the value entered in patient rectum maximum field 516 and then returns back to the value entered in patient rectum minimum field 518, a single rectum cycle is complete.

Similarly, the numeric values entered in patient anus maximum field 520 and patient anus minimum field 522 are the maximum and minimum values used for anal muscle performance analysis and are used to determine a number of anal cycles completed. For example, the patient anus muscle performance value starts from the value entered in patient anus minimum field 522. When the patient anus muscle performance value reaches the value entered in patient anus maximum field 520 and then returns back to the value entered in patient anus minimum field 522, a single anal cycle is complete.

Constipation mode radio button 524 and incontinence mode radio button 526 allow the user to toggle between the anal analysis modes. Selection of update record button 528 by the user causes presentation of another user interface window, which allows the user to update the information that was previously entered for the patient. Selection of analysis button 530 after entering the data requested for the patient causes interfaced computing device 310 to enter the analysis mode. Selection of save button 532 saves data collected during the analysis mode, for example, to database 318. In the illustrative embodiment, save button 532 is disabled until an analysis has been performed.

Figure 6:
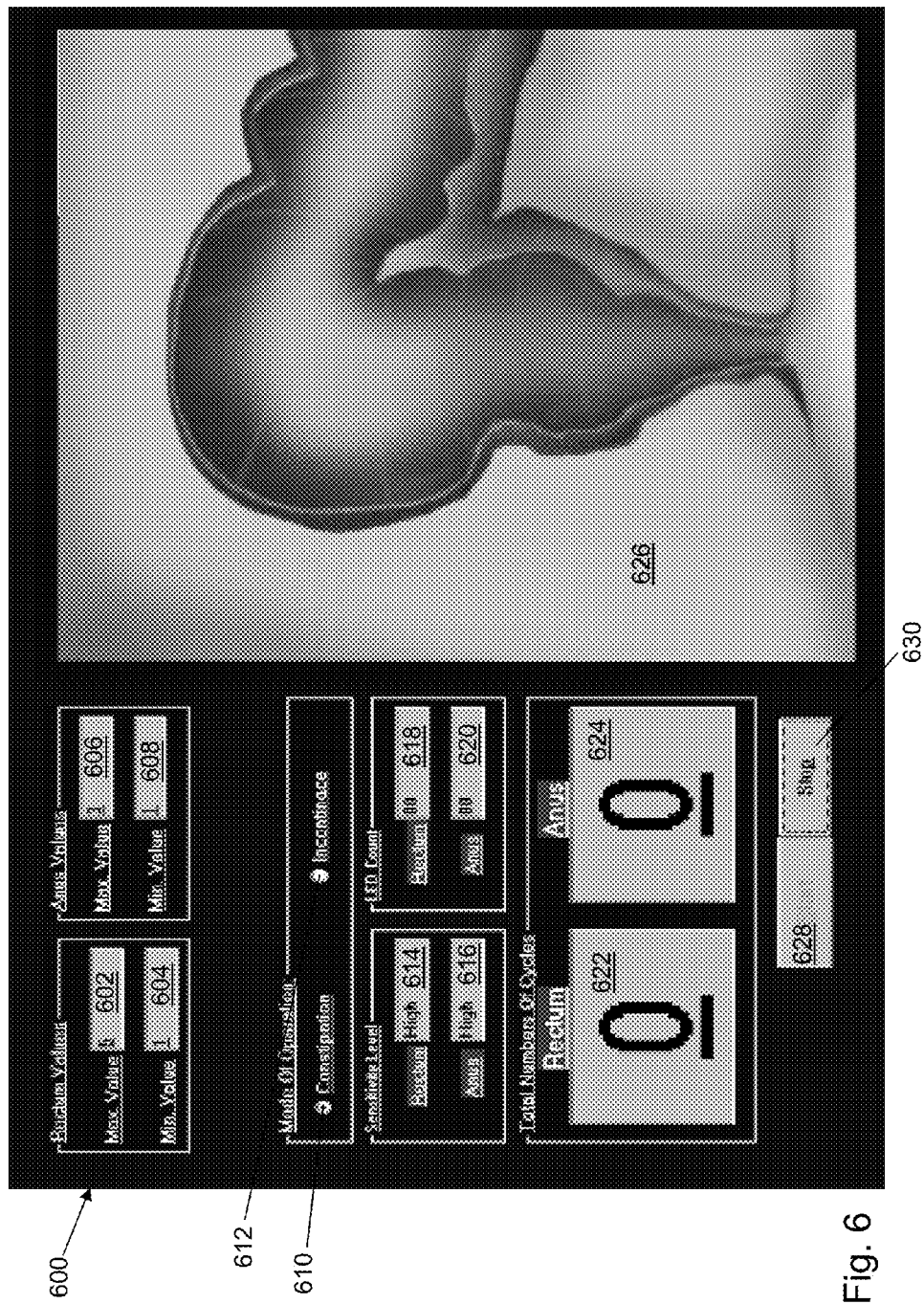
FIG. 6 is a second user interface window presented under control of the biofeedback performance application of the interfaced computing device of FIG. 3 in accordance with an illustrative embodiment.

In an illustrative embodiment, selection of analysis button 530 may cause presentation of a second user interface window 600 on display 312 shown with reference to FIG. 6. Second user interface window 600 may include a rectum maximum field 602, a rectum minimum field 604, an anal maximum field 606, an anal minimum field 608, a second constipation mode radio button 610, a second incontinence mode radio button 612, a rectum sensitivity level field 614, an anal sensitivity level field 616, a rectum LED count field 618, an anal LED count field 620, a rectum cycle count field 622, an anal cycle count field 624, a muscle performance image 626, a start button 628, and a stop button 630. Rectum maximum field 602, rectum minimum field 604, anal maximum field 606, and anal minimum field 608 indicate the values entered/selected by the user in first user interface window 500. Depending on the embodiment, the user may or may not be able to change the values presented in rectum maximum field 602, rectum minimum field 604, anal maximum field 606, and anal minimum field 608.

Similarly, second constipation mode radio button 610 and second incontinence mode radio button 612 indicate the selections by the user in first user interface window 500 and/or selected using anal mode selector button 428. Depending on the embodiment, the user may or may not be able to change the values presented in second constipation mode radio button 610 and second incontinence mode radio button 612.

The rectum sensitivity level selected using rectal sensitivity selector button 406 is presented in rectum sensitivity level field 614. The anal sensitivity level selected using anal sensitivity selector button 418 is presented in anal sensitivity level field 616. Depending on the embodiment, the user may or may not be able to change the values presented in rectum sensitivity level field 614 and anal sensitivity level field 616.

Rectum LED count field 618 may indicate the number of LEDs switched on in rectal muscle output indicator 414 of monitor 104. Anal LED count field 620 may indicate the number of LEDs switched on in anal muscle output indicator 424 of monitor 104. Rectum cycle count field 622 and anal cycle count field 624 indicate the number of rectal and anal cycles completed by the patient using probe 102, respectively.

Muscle performance image 626 displays a visualization of the rectum muscle movement and/or the anal muscle movement so that the user can visualize the muscle relaxation and contraction while using biofeedback training system 100. Muscle performance image 626 is changed based on the pressure levels measured by rectal muscle pressure sensor 220 and/or anal muscle pressure sensor 222. For example, FIGS. 7a-7i depict anus muscle movement for the constipation mode presented under control of biofeedback performance application 310 of interfaced computing device 106 in accordance with an illustrative embodiment; FIGS. 8a-8i depict anus muscle movement for the incontinence mode presented under control of biofeedback performance application 310 of interfaced computing device 106 in accordance with an illustrative embodiment; and FIGS. 9a-9k depict a rectal muscle movement presented under control of biofeedback performance application 310 of interfaced computing device 106 in accordance with an illustrative embodiment.

After powering on monitor 104 and inserting probe 102, start button 628 can be selected to start the analysis process. The cycles are counted as the patient uses the device. After completing the analysis, stop button 630 can be selected to stop the analysis process. After closing second user interface window 600, save button 532 may be selected to save the data collected during the analysis mode.

As used in this disclosure, the term "mount" includes join, unite, connect, associate, insert, hang, hold, affix, attach, fasten, bind, paste, secure, bolt, screw, rivet, solder, weld, glue, form over, layer, and other like terms. The phrases "mounted on" and "mounted to" include any interior or exterior portion of the support member referenced. These phrases also encompass direct mounting (in which the referenced elements are in direct contact) and indirect mounting (in which the referenced elements are not in direct contact).

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise. The illustrative embodiments may be implemented as a method, apparatus, or article of manufacture using standard programming and/or engineering techniques to produce software, firmware, hardware, or any combination thereof to control a computer to implement the disclosed embodiments.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A probe comprising:
   a housing configured for insertion into a rectum, the housing having an insertion end and a non-insertion end;
   a rectal muscle air bag, wherein the rectal muscle air bag is mounted to the housing a first distance from the non-insertion end, wherein the first distance is selected to position the rectal muscle air bag adjacent a rectal muscle when the housing is inserted in the rectum;
   a rectal tube connected to the rectal muscle air bag at a first end of the rectal tube to provide a first vent for the rectal muscle air bag, wherein the rectal tube is further configured for connection to a first pressure sensor at a second end of the rectal tube;
   an anal muscle air bag, wherein the anal muscle air bag is mounted to the housing a second distance from the non-insertion end, wherein the second distance is selected to position the anal muscle air bag adjacent an anal muscle when the housing is inserted in the rectum;
   an anal tube connected to the anal muscle air bag at a first end of the anal tube to provide a first vent for the anal muscle air bag, wherein the anal tube is further configured for connection to a second pressure sensor at a second end of the anal tube;
   a stool stimulation air bag mounted to the housing at the insertion end;
   a stool stimulation tube connected to the stool stimulation air bag at a first end of the stool stimulation tube to provide a first vent for the stool stimulation air bag, wherein the stool stimulation tube is further configured for connection to a fluid source at a second end of the stool stimulation tube; and
   a valve connected to the stool stimulation tube and configured to control a flow of fluid into the stool stimulation tube.

2. The probe of claim 1, wherein the valve is further configured to allow deflation of the stool stimulation air bag when pressure is exerted on the stool stimulation air bag.

3. The probe of claim 1, further comprising a stop edge extending from the housing near the non-insertion end, wherein the stop edge is sized to prevent insertion of the probe into the rectum beyond the stop edge.

4. The probe of claim 1, further comprising the first pressure sensor configured to measure a rectal muscle pressure and the second pressure sensor configured to measure an anal muscle pressure.

5. A system comprising:
a housing;
a first pressure sensor mounted to the housing and configured to measure a rectal muscle pressure;
a second pressure sensor mounted to the housing and configured to measure an anal muscle pressure;
a probe comprising
a probe housing configured for insertion into a rectum, the probe housing having an insertion end and a non-insertion end;
a rectal muscle air bag, wherein the rectal muscle air bag is mounted to the probe housing a first distance from the non-insertion end, wherein the first distance is selected to position the rectal muscle air bag adjacent a rectal muscle when the probe housing is inserted in the rectum;
a rectal tube connected to the rectal muscle air bag at a first end of the rectal tube and to the first pressure sensor at a second end of the rectal tube;
an anal muscle air bag, wherein the anal muscle air bag is mounted to the probe housing a second distance from the non-insertion end, wherein the second distance is selected to position the anal muscle air bag adjacent an anal muscle when the probe housing is inserted in the rectum; and
an anal tube connected to the anal muscle air bag at a first end of the anal tube and to the second pressure sensor at a second end of the anal tube;
a processor mounted to the housing and configured to control presentation of the measured rectal muscle pressure and the measured anal muscle pressure; and
a mode button mounted to the housing and configured to allow selection of a measurement mode, wherein a first mode for selection is a constipation mode and a second mode for selection is an incontinence mode.

6. The system of claim 5, wherein when the first mode is selected, the rectal muscle pressure measurement and the anal muscle pressure measurement are measured when pressure is released on rectal muscle air bag and anal muscle air bag, respectively.

7. The system of claim 5, wherein when the second mode is selected, the rectal muscle pressure measurement and the anal muscle pressure measurement are measured when pressure is applied to rectal muscle air bag and anal muscle air bag, respectively.

8. The system of claim 5, wherein the measured rectal muscle pressure and the measured anal muscle pressure are presented simultaneously.

9. The system of claim 5, further comprising a stool stimulation air bag mounted to the housing at the insertion end.

10. The system of claim 5, further comprising a sensitivity button mounted to the housing and configured to allow selection of a sensitivity level for the rectal muscle pressure measurement.

11. The system of claim 10, wherein the presentation of the measured rectal muscle pressure comprises a row of lights mounted to the housing, wherein a number of lights turned on in the row of lights, $R_r$, is calculated based on $R_r=(ADC_r-A_{0r})/2S_r$, where $ADC_r$ is a digital value of the received rectal muscle pressure, $A_{0r}$ is an auto zero value for the first pressure sensor, and $S_r$ is a numerical value associated with the sensitivity level selected using the sensitivity button.

12. The system of claim 5, wherein the presentation of the measured rectal muscle pressure comprises a first row of lights mounted to the housing, wherein a number of lights turned on in the first row of lights is selected based on the rectal muscle pressure measurement.

13. The system of claim 12, wherein the presentation of the measured anal muscle pressure comprises a second row of lights mounted to the housing, wherein a number of lights turned on in the second row of lights is selected based on the anal muscle pressure measurement.

14. The system of claim 5, further comprising a sensitivity button mounted to the housing and configured to allow selection of a sensitivity level for the anal muscle pressure measurement.

15. The system of claim 14, wherein the presentation of the measured anal muscle pressure comprises a row of lights mounted to the housing, wherein a number of lights turned on in the row of lights, $R_a$, is calculated based on $R_a=(A_{0a}-ADC_a)/S_a$, where $ADC_a$ is a digital value of the received anal muscle pressure, $A_{0a}$ is an auto zero value for the second pressure sensor, and $S_a$ is a numerical value associated with the sensitivity level selected using the sensitivity button.

16. The system of claim 14, wherein the presentation of the measured anal muscle pressure comprises a row of lights mounted to the housing, wherein a number of lights turned on in the row of lights, $R_a$, is calculated based on $R_a=(ADC_a-A_{0a})/S_a$, where $ADC_a$ is a digital value of the received anal muscle pressure, $A_{0a}$ is an auto zero value for the second pressure sensor, and $S_a$ is a numerical value associated with the sensitivity level selected using the sensitivity button.

17. The system of claim 16, wherein $S_a$ further includes a second numerical value associated with a second sensitivity level selected by a clinician.

18. A system comprising:
a first housing;
a first pressure sensor mounted to the first housing and configured to measure a rectal muscle pressure;
a second pressure sensor mounted to the first housing and configured to measure an anal muscle pressure;
a probe comprising
a probe housing configured for insertion into a rectum, the probe housing having an insertion end and a non-insertion end;
a rectal muscle air bag, wherein the rectal muscle air bag is mounted to the probe housing a first distance from the non-insertion end, wherein the first distance is selected to position the rectal muscle air bag adjacent a rectal muscle when the probe housing is inserted in the rectum;
a rectal tube connected to the rectal muscle air bag at a first end of the rectal tube and to the first pressure sensor at a second end of the rectal tube;
an anal muscle air bag, wherein the anal muscle air bag is mounted to the probe housing a second distance from the non-insertion end, wherein the second distance is selected to position the anal muscle air bag adjacent an anal muscle when the probe housing is inserted in the rectum; and
an anal tube connected to the anal muscle air bag at a first end of the anal tube and to the second pressure sensor at a second end of the anal tube; and
a first processor mounted to the first housing and configured to control presentation of the measured rectal muscle pressure and the measured anal muscle pressure;
a first communication interface operably coupled to the first processor and configured to send the measured rectal muscle pressure and the measured anal muscle pressure to a second communication interface;
a second processor mounted to a second housing;
the second communication interface operably coupled to the second processor and configured to receive the measured rectal muscle pressure and the measured anal muscle pressure from the first communication interface; and a computer-readable medium operably coupled to the second processor, the computer-readable medium having computer-readable instructions stored thereon that, when executed by the second processor, cause the system to control presentation of a graphical representation of the received rectal muscle pressure and the received anal muscle pressure in a display.

19. The system of claim 18, wherein the graphical representation includes a visualization of movement of the rectum muscle based on the received rectal muscle pressure.

20. The system of claim 18, wherein the graphical representation includes a visualization of movement of the anal muscle based on the received anal muscle pressure.

21. The system of claim 18, wherein the computer-readable instructions further cause the system to:
control presentation of a user interface window in the display, wherein the user interface window includes a patient identifier field; and
receive a patient identifier entered in the patient identifier field.

22. The system of claim 21, wherein the user interface window further includes a patient rectum maximum field and a patient rectum minimum field and further wherein the computer-readable instructions further cause the system to:
receive a rectum maximum value entered in the patient rectum maximum field;
receive a rectum minimum value entered in the patient rectum minimum field; and
determine a number of rectal cycles completed by comparing the measured rectal muscle pressure to the received rectum maximum value and the received rectum minimum value, wherein the determined number of rectal cycles completed is associated with the received patient identifier.

23. The system of claim 22, wherein the computer-readable instructions further cause the system to control presentation of the determined number of rectal cycles completed in the display.

24. The system of claim 21, wherein the user interface window further includes a patient anal maximum field and a patient anal minimum field and further wherein the computer-readable instructions further cause the system to:
receive an anal maximum value entered in the patient anal maximum field;
receive an anal minimum value entered in the patient anal minimum field; and
determine a number of anal cycles completed by comparing the measured anal muscle pressure to the received anal maximum value and the received anal minimum value, wherein the determined number of anal cycles completed is associated with the received patient identifier.

25. The system of claim 24, wherein the computer-readable instructions further cause the system to control presentation of the determined number of anal cycles completed in the display.

26. The system of claim 21, wherein the user interface window further includes a mode field configured to allow selection of a measurement mode, wherein a first mode for selection is a constipation mode and a second mode for selection is an incontinence mode, and further wherein the computer-readable instructions further cause the system to receive a mode selection indicator entered using the mode field, wherein the mode selection indicator is associated with the received patient identifier.

27. The system of claim 26, wherein the mode field is implemented as a radio button.

28. The system of claim 26, wherein the computer-readable instructions further cause the system to send information associated with the mode selection indicator to the first communication interface using the second communication interface.

29. The system of claim 28, further comprising a mode button mounted to the first housing and configured to indicate a mode selection based on the received information associated with the mode selection indicator.

30. The system of claim 21, wherein the user interface window further includes a rectum sensitivity level field configured to allow selection of a measurement sensitivity level for a rectal muscle, and further wherein the computer-readable instructions further cause the system to receive a rectum sensitivity level indicator entered using the rectum sensitivity level field, wherein the rectum sensitivity level indicator is associated with the received patient identifier.

31. The system of claim 30, wherein the computer-readable instructions further cause the system to send information associated with the rectum sensitivity level indicator to the first communication interface using the second communication interface.

32. The system of claim 31, further comprising a sensitivity button mounted to the first housing and configured to indicate a sensitivity level for the rectal muscle pressure measurement based on the received information associated with the rectum sensitivity level indicator.

33. The system of claim 21, wherein the user interface window further includes an anal sensitivity level field configured to allow selection of a measurement sensitivity level for an anal muscle, and further wherein the computer-readable instructions further cause the system to receive an anal sensitivity level indicator entered using the anal sensitivity level field, wherein the anal sensitivity level indicator is associated with the received patient identifier.

34. The system of claim 33, wherein the computer-readable instructions further cause the system to send information associated with the anal sensitivity level indicator to the first communication interface using the second communication interface.

35. The system of claim 34, further comprising a sensitivity button mounted to the first housing and configured to indicate a sensitivity level for the anal muscle pressure measurement based on the received information associated with the anal sensitivity level indicator.

36. The system of claim 21, wherein the user interface window further includes a rectum light count field configured to allow selection of a number of lights to use for presentation of a rectal muscle output indicator, and further wherein the computer-readable instructions further cause the system to receive a rectum light count indicator entered using the rectum light count field, wherein the rectum light count indicator is associated with the received patient identifier.

37. The system of claim 36, wherein the computer-readable instructions further cause the system to send information associated with the rectum light count indicator to the first communication interface using the second communication interface.

38. The system of claim 37, further comprising a row of lights mounted to the first housing, wherein the first processor is configured to control presentation of the measured rectal muscle pressure using a number of lights turned on in the row of lights selected based on the rectal muscle pressure measurement and the rectum light count indicator.

39. The system of claim 21, wherein the user interface window further includes an anal light count field configured to allow selection of a number of lights to use for presentation of an anal muscle output indicator, and further wherein the computer-readable instructions further cause the system to receive an anal light count indicator entered using the anal light count field, wherein the anal light count indicator is associated with the received patient identifier.

40. The system of claim 39, wherein the computer-readable instructions further cause the system to send information associated with the anal light count indicator to the first communication interface using the second communication interface.

41. The system of claim 40, further comprising a row of lights mounted to the first housing, wherein the first processor is configured to control presentation of the measured anal muscle pressure using a number of lights turned on in the row of lights selected based on the anal muscle pressure measurement and the anal light count indicator.

* * * * *